United States Patent [19]

Reiner

[11] 4,268,685

[45] May 19, 1981

[54] SALICYLAMIDE ESTERS AND RELATED PHARMACEUTICAL COMPOSITION

[75] Inventor: Alberto Reiner, Como, Italy

[73] Assignee: Neopharmed S.p.A., Milan, Italy

[21] Appl. No.: 129,660

[22] Filed: Mar. 12, 1980

[30] Foreign Application Priority Data

Mar. 27, 1979 [IT] Italy ............................... 21320 A/79

[51] Int. Cl.³ ............................................ C07C 69/76
[52] U.S. Cl. ......................................... 560/56; 560/47;
560/48; 560/105; 560/55; 424/263; 424/309;
424/308; 424/310; 546/310
[58] Field of Search ...................... 560/55, 56, 47, 48,
560/105; 546/310; 424/309, 310, 308, 263

[56] References Cited

U.S. PATENT DOCUMENTS

| | | | |
|---|---|---|---|
| 3,313,848 | 4/1967 | Scherrer et al. | 560/48 |
| 3,511,873 | 5/1970 | Picciola | 560/48 |
| 3,652,762 | 3/1972 | Sallmann et al. | 560/48 |
| 3,657,430 | 4/1972 | Shen | 560/105 |
| 3,673,243 | 6/1972 | Yamamoto et al. | 560/48 |
| 3,778,470 | 12/1973 | Sallmann | 560/48 |
| 4,029,815 | 6/1977 | Sherlock et al. | 560/47 |
| 4,049,699 | 9/1977 | Sinkula | 560/48 |
| 4,049,700 | 9/1977 | Sinkula | 560/105 |
| 4,150,137 | 4/1979 | Noda et al. | 560/105 |
| 4,198,431 | 4/1980 | Kato | 560/47 |

FOREIGN PATENT DOCUMENTS 47-25336  7/1972  Japan ................................. 560/47
49-30340  3/1974  Japan ................................. 560/48
52-20467  6/1977  Japan ................................. 560/48

*Primary Examiner*—Paul J. Killos
*Attorney, Agent, or Firm*—Murray & Whisenhunt

[57] ABSTRACT

Esters of salicylamide with anti-inflammatory and analgesic action are disclosed.

These esters have the following general formula:

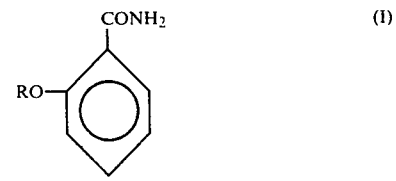

(I)

wherein R is a radical of an acid selected among d-2-(6'-methoxy-2'-naphtyl)-propionic acid, 2[[3-(trifluoromethyl)phenyl]-amino]-3-pyridine carboxylic acid, 2- {[3-(trifluoromethyl)-phenyl]-amino}-3-pyridincarboxylic acid, 2-(4-isobutyl-phenyl)-propionic acid, 4-allyloxy-3-chloro-phenylacetic acid, 2-(3-benzoylphenyl)-propionic acid, 2-[(2,3-dimethylphenyl)amino]-benzoic acid and 2[[3-trifluoromethyl)phenyl]-amino]benzoic acid.

The process for preparing the subject esters comprises reacting a halide, preferably a chloride of the desired acid, with a solution of salicylamide.

5 Claims, No Drawings

SALICYLAMIDE ESTERS AND RELATED PHARMACEUTICAL COMPOSITION

The present invention relates to esters of salicylamide having anti-inflammatory and analgesic activity. More specifically the present invention relates to esters of salicylamide having the following general formula:

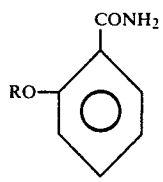

wherein R is a radical of an acid selected amongst d-2-(6'-methoxy-2'-naphtyl)-propionic acid, 2[[3-(trifluoromethyl)phenyl]-amino]-3-pyridine carboxylic acid, 2-{[3-(trifluoromethyl)-phenyl]-amino}-3-pyridincarboxylic acid, 2-(4-isobutyl-phenyl)-propionic acid, 4-allyloxy-3-chloro-phenylacetic acid, 2-(3-benzoyl-phenyl)-propionic acid, 2-[(2,3-dimethylphenyl)amino]-benzoic acid and 2[[3-trifluoromethyl)phenyl]-amino]-benzoic acid.

In fact it has been found that the compounds of the present invention, besides the effective anti-inflammatory and analgesic action, are also endowed with a time extended effect (greater time of release) and have a reduced ulcerogenic action on the gastric mucous membrane. Although the action mechanism as hereinafter described should not be considered as a compulsory explanation of the pharmacological results of the compounds of the present invention, it seems acceptable the explanation according to which:

(a) the esterification of the acid, having the anti-inflammatory activity, is responsible of the reduced ulcerogenic activity and (b) the salicylamide, which is mainly responsible of the analgesic action, after the administration is not present in the plasma, whereby the molecule should act in toto, without any esterase action involving the decomposition thereof.

In turn, the process of the present invention for the preparation of the esters having the preceding formula (I) comprises reacting the salicylamide, in form of a solution in a suitable solvent, with a halide, particularly the chloride of the desired acid, by slowly supplementing the solution of salicylamide with the halide, under stirring and by permitting the reaction mixture to spontaneously heat up to a controlled temperature, the reaction mixture being then heated to a predetermined temperature and maintained at such a temperature for a predetermined time period, and the reaction product is then isolated from the reaction mixture and purified or the pharmaceutical use. The particular features of the process of the present invention shall more clearly appear from the following examples, having illustrative but non limiting purpose, referred to some of the compounds as contemplated by the present invention.

EXAMPLE 1

Ester of salicylamide with 2-(6'-methoxy-2'-naphtyl)-propionic acid

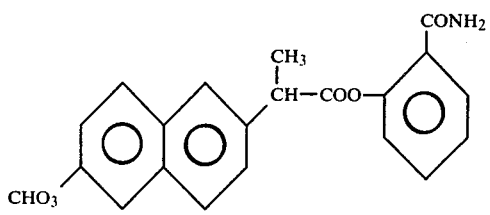

13.7 g of salicylamide are dissolved in 60 mls pyridine; the solution is supplemented with 28 g portions of chloride of d-2-(6'-methoxy-2'-naphtyl)-propionic acid, by externally cooling with water, so as to keep the reaction mixture below 20° C.

At the end of the addition the mixture is gradually heated up to 45° C. and then maintained standing at room temperature for a night. After filtration, the solution is concentrated to dryness, the oil residue being taken with water and dispersed; after filtration of the water there is obtained a rubber product which is taken with a small amount of acetone, thus forming a solution. The latter is slowly poured in water made alkaline with a small amount of NaHCO₃: there is formed a partially crystalline and partially rubbery mass which, after separation, is twice washed with water made acidic by means of HCl. For the complete crystallization the dispersion in water, made alkaline with NaHCO₃, and the filtration are repeated.

There are obtained 26 g of raw product, which is first crystallized from ethyl alcohol and then from benzene, giving place to an essentially pure product, having melting point of 117°-120° C.

The product is soluble in acetone and pyridine, little soluble in chloroform, alcohol and benzene, and insoluble in water.

EXAMPLE 2

Ester of salicylamide with 4-allyloxy-3-chlorophenylacetic acid,

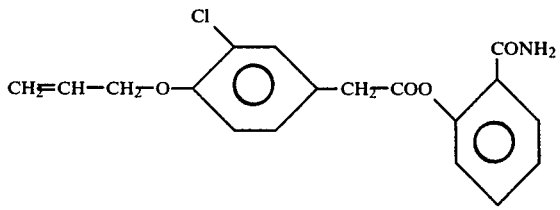

65 g (0.49 moles) of salicylamide are dissolved in 200 mls of chloroform and the solution is charged in a flask.

The solution is dropwise supplemented with 152 g (0.62 moles) of chloride of 4-allyloxy-3-chlorophenylacetic acid and with 63 g of triethylamine in about 30 minutes. The reaction mixture is spontaneously heated from 20° C. to 60° C.

Then the reaction mixture is refluxed for 3 hours, giving place to a dark red, cloudy solution. After cooling to 20° C., the reaction mixture is poured in 500 mls of cold water, under stirring. After separation, the washing with 500 mls of water is repeated, the washing water being at pH 7. The reaction product is separated, dried on Na₂SO₄, filtered and concentrated under vacuum.

The still hot oily mass, of red colour, is supplemented with 250 mls of MeOH and cooled. After filtration from the methanol, there are obtained 123 g (in the wet condition) of product. It is crystallized from 60 mls of chloroform and, after filtration, washed with methanol. There are obtained 41 g of product containing light traces of salicylamide (as revealed by chromatography with ferric chloride). The yield is 25%. 6 g of nearly pure product are further recovered by concentrating the residual water.

The final product has a melting point of 150°–152° C. and the analysis for $C_{18}H_{16}O_4NCl$ gives the following results:

calculated: C% 62.5; H% 4.6; N% 4.0; (O+Cl)% 28.7:

found: C% 63.12; H% 5.00; N% 3.80; (O+Cl)% 28.08.

EXAMPLE 3

Ester of salicylamide with 2-(4-isobutyl-phenyl)-propionic acid

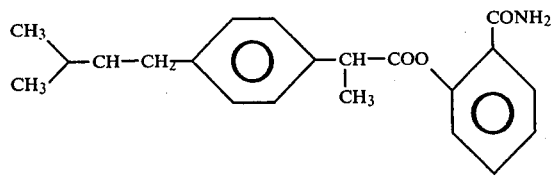

In a flask containing 50 mls of pyridine 52 g of salicylamide are charged, a clear solution being obtained through a light heating. To this solution 92 g of the chloride of the 2-(4-isobutyl-phenyl)-propionic acid are dropwise added, under stirring, with a spontaneous heating from 20° C. to 50° C. The addition, which is completed within about 15 minutes, gives place to a precipitate. The reaction mixture is heated for 90 minutes at a maximum temperature of 80° C. and then cooled down to room temperature, a precipitate of pyridine hydrochloride being formed at about 20° C. The mixture is poured in 700 mls of cold water under stirring, a very fine and dense precipitate being thus formed, which is maintained under stirring for 15 minutes further.

The mixture is decanted and the aqueous phase is separated. The residue is supplemented with further 700 mls of water and stirred for further 15 minutes. There are thus obtained hard, crystalline blocks which must be crushed in a mortar. The pyridine is removed by maintaining the product in water (300 mls) under stirring. The mixture is filtered under reduced pressure and the precipitate is poured in a beaker containing 200 mls of methanol, the mixture being heated for the homogenization. After filtration and crystallization from 800 mls of methanol, there are obtained 62 g of ester. The methanolic liquors are concentrated giving place to further 20 g of product which, after further crystallization, result in 10 g of dry product.

Total yield: 72 g of ester (58.2%).

The product, having melting point of 165°–168° C., has the following analysis for $C_{20}H_{23}NO_3$:

calculated: C% 73.8; H% 7.1; N% 4.3; O% 14.7: found: C% 73.68; H% 7.10; N% 4.22; O% 15.

The pharmacological tests, as carried out with the compound of example 3, show:

(a) a high activity at the hot plate test (b) a time extended action. In this connection, the free acid, namely 2-(4-isobutyl-phenyl)-propionic acid, (also known as Ibuprofen) has a plasma absorption peak 1 hour after the administration, the bioavailability falling down 3 hours after the administration. On the contrary, the diagram of bioavailability (i.e. plasma content) of the compound 3 is maximum one hour after the oral administration and remains essentially unchanged for more than 7 hours.

Another interesting property of the compound of the example 3 is that the forming of prostaglandine synthetases is enhanced, whereas the opposite behaviour is found with the free acid as well as with indomethacin: it might be another reason explaining the greater gastric tolerability of the compounds of the invention.

As regards the pharmaceutical compositions, for which dosages are foreseen of 250 to 500 mg for unitary doses, the compounds of the present invention can be formulated as preparations for oral use, as well as in form of suppositories, the compounds being admixed with or dissolved in suitable vehicles or solvents, to prepare capsules, tablets, pills, soft gelatin capsules, solutions for dropwise administration, solutions and suppositories.

The preparations can also be formulated in form suitable for time delayed release.

I claim:

1. Esters of salicylamide having the general formula:

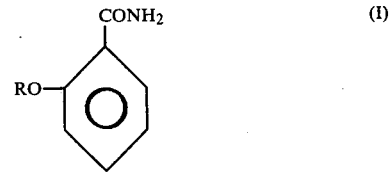

wherein R is a radical of an acid selected amongst d-2-(6'-methoxy-2'-naphtyl)-propionic acid, 2[[3-(trifluoromethyl)phenyl]-amino]-3 pyridine carboxylic acid, 2-{[3-(trifluoromethyl)-phenyl]-amino}-3-pyridincarboxylic acid, 2-(4-isobutyl-phenyl)-propionic acid, 4-allyloxy-3-chloro-phenylacetic acid, 2-(3-benzoylphenyl)-propionic acid, 2[(2,3-dimethylphenyl)amino]-benzoic acid and 2-[[3-trifluoromethyl)phenyl]-amino]-benzoic acid.

2. Ester of salicylamide of d-2-(6'-methoxy-2'-naphtyl)-propionic acid according to claim 1.

3. Ester of salicylamide of 2-(4-isobutyl-phenyl)-propionic acid according to claim 1.

4. Ester of salicylamide of 4-allyloxy-3-chloro-phenyl-acetic acid according to claim 1.

5. Pharmaceutical composition, particularly for the therapy of inflammatory and painful states, characterized by containing, as the active ingredient, a salicylamide ester according to claim 1 or according to each claim 2, 3 or 4, together with suitable carriers and eccipients.

* * * * *